US010932876B2

(12) United States Patent
Levy et al.

(10) Patent No.: US 10,932,876 B2
(45) Date of Patent: Mar. 2, 2021

(54) HAPTIC FEEDBACK DEVICE, SYSTEM AND METHOD FOR OPERATION OF A MEDICAL TOOL

(71) Applicant: Biosense Webster (Israel) Ltd., Yokneam (IL)

(72) Inventors: Dror Shlomo Levy, Irvine, CA (US); Yevgeny Bonyak, Haifa (IL); Boris Ashkinezer, Akko (IL); Oleg Dulger, Zichron Yaakov (IL); Doron Moshe Ludwin, Haifa (IL); Moshe Ingel, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 160 days.

(21) Appl. No.: 16/117,961

(22) Filed: Aug. 30, 2018

(65) Prior Publication Data
US 2019/0201151 A1    Jul. 4, 2019

Related U.S. Application Data

(60) Provisional application No. 62/611,228, filed on Dec. 28, 2017.

(51) Int. Cl.
*A61B 34/00* (2016.01)
*A61B 18/14* (2006.01)
(Continued)

(52) U.S. Cl.
CPC .............. *A61B 34/76* (2016.02); *A61B 5/065* (2013.01); *A61B 5/283* (2021.01); *A61B 5/6852* (2013.01);
(Continued)

(58) Field of Classification Search
USPC .................................................. 600/508–509
See application file for complete search history.

(56) References Cited

U.S. PATENT DOCUMENTS 5,391,199 A    2/1995  Ben-Haim
5,443,489 A    8/1995  Ben-Haim
(Continued)

FOREIGN PATENT DOCUMENTS

EP    2777585 A1    9/2014

OTHER PUBLICATIONS

Extended European Search Report dated May 17, 2019 for the European Patent Application No. 18275260.0.

*Primary Examiner* — Nicole F Lavert (57) ABSTRACT

A haptic feedback device receives a signal reflecting pressure exerted by a medical tool against an anatomical surface. A fastener secures the feedback device to, for example, a wrist of an operator. A haptic exertion component exerts haptic stimulation to the operator based on the received signal such that when the received signal reflects a pressure being exerted by the medical tool against the anatomical surface of a patient is in a defined range for operation of the medical tool, the exertion component exerts haptic stimulation at a predetermined level that indicates pressure of the medical tool is being exerted in the defined range. Otherwise, the exertion component does not exert a level of haptic stimulation that is equal to or more than the predetermined level or the exertion component exerts a level of haptic stimulation to the operator that is more than the predetermined level.

20 Claims, 4 Drawing Sheets

(51) Int. Cl.
*A61B 5/00* (2006.01)
*A61B 5/283* (2021.01)
*A61B 90/53* (2016.01)
*A61B 5/06* (2006.01)
*A61B 90/00* (2016.01)
*A61B 18/00* (2006.01)
*A61B 17/00* (2006.01)
*A61B 34/20* (2016.01)

(52) U.S. Cl.
CPC .......... *A61B 5/6885* (2013.01); *A61B 5/7455* (2013.01); *A61B 18/1492* (2013.01); *A61B 90/53* (2016.02); *A61B 2017/00053* (2013.01); *A61B 2017/00199* (2013.01); *A61B 2017/00221* (2013.01); *A61B 2018/00303* (2013.01); *A61B 2018/00351* (2013.01); *A61B 2018/00357* (2013.01); *A61B 2018/00577* (2013.01); *A61B 2018/00839* (2013.01); *A61B 2034/2046* (2016.02); *A61B 2090/065* (2016.02)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,690,963 B2 | 2/2004 | Ben-Haim et al. |
| 6,788,967 B2 | 9/2004 | Ben-Haim et al. |
| 9,636,164 B2 | 5/2017 | Panescu et al. |
| 2006/0100610 A1 | 5/2006 | Wallace et al. |
| 2009/0093806 A1 | 4/2009 | Govari et al. |
| 2009/0138007 A1 | 5/2009 | Govari et al. |
| 2009/0247993 A1 | 10/2009 | Kirschenman et al. |
| 2010/0073150 A1 | 3/2010 | Olson et al. |
| 2010/0312129 A1 | 12/2010 | Schecter |
| 2014/0022162 A1* | 1/2014 | Yu ............... A61N 5/06 345/156 |
| 2015/0127738 A1* | 5/2015 | Thompson ....... H04W 4/80 709/204 |
| 2015/0157399 A1 | 6/2015 | Romoscanu |
| 2017/0178471 A1* | 6/2017 | Levesque ........... A41D 1/002 |

\* cited by examiner

HAPTIC FEEDBACK DEVICE, SYSTEM AND METHOD FOR OPERATION OF A MEDICAL TOOL

CROSS REFERENCE TO RELATED APPLICATION

The present application is a non-provisional of Provisional Application No. 62/611,228 filed Dec. 28, 2017 which is incorporated herein by reference as if fully set forth.

SUMMARY

A haptic feedback device is provided for use with a medical tool that includes a pressure sensor wherein the medical tool requires a predetermined degree of contact with an anatomical surface of a patient to properly operate. In this context, the medical tool's sensor generates a sensor signal reflecting an amount of pressure exerted by the medical tool against the anatomical surface with which the tool is being used.

In one example, the haptic feedback device includes a fastener configured to secure the haptic feedback device to a desired position on an operator of the medical tool. The haptic feedback device includes a signal input configured to receive a signal reflective of the tool's sensor signal. A haptic exertion component is configured to exert multiple levels of haptic stimulation to the operator upon a condition that haptic feedback device is secured to the desired position on the medical tool's operator by the fastener.

The haptic feedback device is configured to control the level of haptic stimulation exerted based on the signal received by the signal input such that when the received signal reflects a pressure being exerted by the medical tool against the anatomical surface of the patient is in a defined range of pressure selected for operation of the medical tool, the exertion component exerts haptic stimulation to the operator at a predetermined level that indicates pressure of the medical tool is being exerted in the defined range. The haptic feedback device is also configured to control the level of haptic stimulation exerted such that when the received signal reflects a pressure being exerted by the medical tool against the anatomical surface of the patient is less than the defined range, the exertion component does not exert a level of haptic stimulation to the operator that is equal to or more than the predetermined level. The haptic feedback device is further configured to control the level of haptic stimulation exerted based on the signal received by the signal input such that when the received signal reflects a pressure being exerted by the medical tool against the anatomical surface of the patient is more than the defined range, the exertion component exerts a level of haptic stimulation to the operator that is more than the predetermined level.

The haptic feedback device preferably includes a fastener configured to secure the haptic feedback device to a wrist of the operator. In one example, the haptic exertion component is configured to exert vibration as haptic stimulation and includes a vibration component associated with the signal input configured to vibrate the haptic feedback device at different levels of frequency whereby the predetermined level of haptic stimulation is a predetermined level of vibration frequency provided by the vibration component. The vibration component can be disposed in a housing having an associated wrist strap to secure the housing to a wrist of the operator.

In another example, the haptic exertion component is configured to exert pressure as haptic stimulation and includes a pressure applicator connected to a drive mechanism that is configured to selectively drive the pressure applicator based on the signal received by the signal input such that when the haptic feedback device is secured to the desired position on the operator the pressure applicator is able to exert different levels of pressure to the wrist of the operator whereby the predetermined level of haptic stimulation is a predetermined level of pressure exerted by the pressure applicator. Such a pressure exertion component can be disposed in a housing with an associated wrist strap to secure the housing to a wrist of the operator. The drive mechanism may, for example, be configured as a DC step motor. Another example is to use an electro-active polymer in a wrist band or other configuration to apply pressure that is electrically driven.

The defined range may be the entire operational range or a portion of an operational range of the medical tool. When the defined range is a portion of the operational range, the haptic feedback device can be configured to control the level of haptic stimulation exerted based on the signal received by the signal input such that the exertion component exerts haptic stimulation to the operator at the predetermined level in response to a "go" control signal that indicates pressure of the medical tool is being exerted in the defined range, the exertion component exerts a level of haptic stimulation to the operator that is less than the predetermined level in response a "low caution" control signal that indicates a signal generated by the force sensor of less than a low end of the defined range, but within the operational range, and the exertion component exerts a level of haptic stimulation to the operator that is more than the predetermined level in response a "high caution" control signal that indicates a signal generated by the force sensor of more than a high end of the defined range, but within the operational range. In such case, the haptic feedback device can be configured to control the level of haptic stimulation exerted based on the signal received by the signal input such that, when the received signal reflects a pressure being exerted by the medical tool against the anatomical surface of the patient is less than the operational range, the exertion component does not exert a level of haptic stimulation to the operator that is equal to or more than the level exerted in response to the "low caution" control signal, and, when the received signal reflects a pressure being exerted by the medical tool against the anatomical surface of the patient is more than the operational range, the exertion component exerts a level of haptic stimulation to the operator that is more than the level exerted in response to the "low caution" control signal.

Where the defined range is at least a portion of an operational range of the medical tool, the haptic feedback device may be configured to control the level of haptic stimulation exerted based on the signal received by the signal input such that the exertion component exerts a level of haptic stimulation to the operator that is less than the predetermined level in response a "contact" control signal that indicates a non-zero signal generated by the force sensor of less the operational range, and/or the exertion component exerts a level of haptic stimulation to the operator that is more than the predetermined level in response a "stop" control signal that indicates a signal generated by the force sensor of sufficient to cause tissue damage above the operational range.

The haptic feedback device can, in particular, be used with a medical tool that is configured as an ablation tool at the distal end of a catheter. In such case, the range of pressure for which the haptic exertion component is configured to exert the predetermined level of haptic stimulation can be defined based on a desired range of pressure to be applied by the ablation tool to a cardiac surface during an ablation procedure of a beating heart.

Accordingly, a medical system can be provided that includes the haptic feedback device, a catheter including the catheter probe and ablation tool, and a console configured to receive the sensor signal from the pressure sensor of the catheter probe and to generate and communicate the signal reflective of the sensor signal to the haptic feedback device. In such a medical system, the signal input of the haptic feedback device can include a wireless receiver and the console can include a transmitter to communicate the signal reflective of the sensor signal. In one example, the console includes a processor configured to process the sensor signal such that the signal reflective of the sensor signal serves as a control signal to control the level of haptic stimulation exerted by the haptic exertion component.

An example method of using the haptic feedback device includes first securing the haptic feedback device to a desired position, such as on a wrist, of an operator of the medical tool. A signal reflective of the sensor signal is received by the haptic feedback device's signal input. Levels of haptic stimulation are exerted to the operator by the haptic exertion component based on the signal received by the signal input. When the received signal reflects a pressure being exerted by the medical tool against the anatomical surface of the patient is in the defined range, the exertion component exerts haptic stimulation to the operator at the predetermined level. When the received signal reflects a pressure being exerted by the medical tool against the anatomical surface of the patient is less than the defined range, the exertion component does not exert a level of haptic stimulation to the operator that is equal to or more than the predetermined level. When the received signal reflects a pressure being exerted by the medical tool against the anatomical surface of the patient is more than the defined range, the exertion component exerts a level of haptic stimulation to the operator that is more than the predetermined level.

Other methods based corresponding to various configurations of the haptic feedback device may also be used.

Where the medical tool with which the haptic feedback is used is an ablation tool at the distal end of a catheter, the defined range of pressure for which the haptic exertion component exerts the predetermined level of haptic stimulation can be defined based on a desired range of pressure to be applied by the ablation tool to a cardiac surface during an ablation procedure of a beating heart, such as a tool's operational range of 7-20 grams or a portion thereof.

Where the medical tool with which the haptic feedback device is used is an electric potential mapping tool at the distal end of a catheter, the defined range of pressure for which the haptic exertion component exerts the predetermined level of haptic stimulation can be defined based on a desired range of pressure to be applied by the mapping tool to a cardiac surface during a mapping procedure of a beating heart, such as a tool's operational range of 3-7 grams or a portion thereof.

A console can receive the sensor signal from the pressure sensor of the catheter probe and generate and communicate the signal reflective of the sensor signal to the haptic feedback device. The signal input of the haptic feedback device can include a wireless receiver so that the console can wirelessly communicates the signal reflective of the sensor signal. A processor can be used to generate the signal reflective of the sensor signal such that the signal reflective of the sensor signal serves as a control signal to control the level of haptic stimulation exerted by the haptic exertion component.

Other object and advantages of the present invention will be apparent to those skilled in the art from the following description and accompanying drawings.

BRIEF DESCRIPTION OF THE DRAWING(S)

The present embodiments are illustrated by way of example, and not by way of limitation, in the figures of the accompanying drawings.

DETAILED DESCRIPTION

Documents incorporated by reference in the present patent application may include terms that are defined in a manner that conflicts with the definitions made explicitly or implicitly in the present specification. In the event of any conflicts, the definitions in the present specification should be considered to be controlling.

During the course of a medical procedure in an operating room, physicians monitor a number of indications and data. Most of the input provided to physicians is visual and sometimes it is audible. Apart from the use of robotic gloves, rarely are the indications haptic, i.e. indications by sense of touch, such as through vibrations or forces.

The disclosed medical system enables immediate and clear feedback to an operating room physician in a haptic feedback modality. For example, in cardiac procedures, the force level that a physician applies on heart tissue is an important factor. If the force is too low, then mapping and/or ablations are inaccurate or insignificant. If the force is too high, injury to the heart tissue can result. A clear haptic feedback that is delivered from the system to the physician can supply reliable feedback of the pressure a medical tool is applying to an anatomical surface. The haptic feedback can be, for example, based on vibration at different frequency levels or the exertion of different levels of pressure applied based on predefined thresholds. Such haptic feedback provides increased patient safety and physician confidence.

Figure 1:
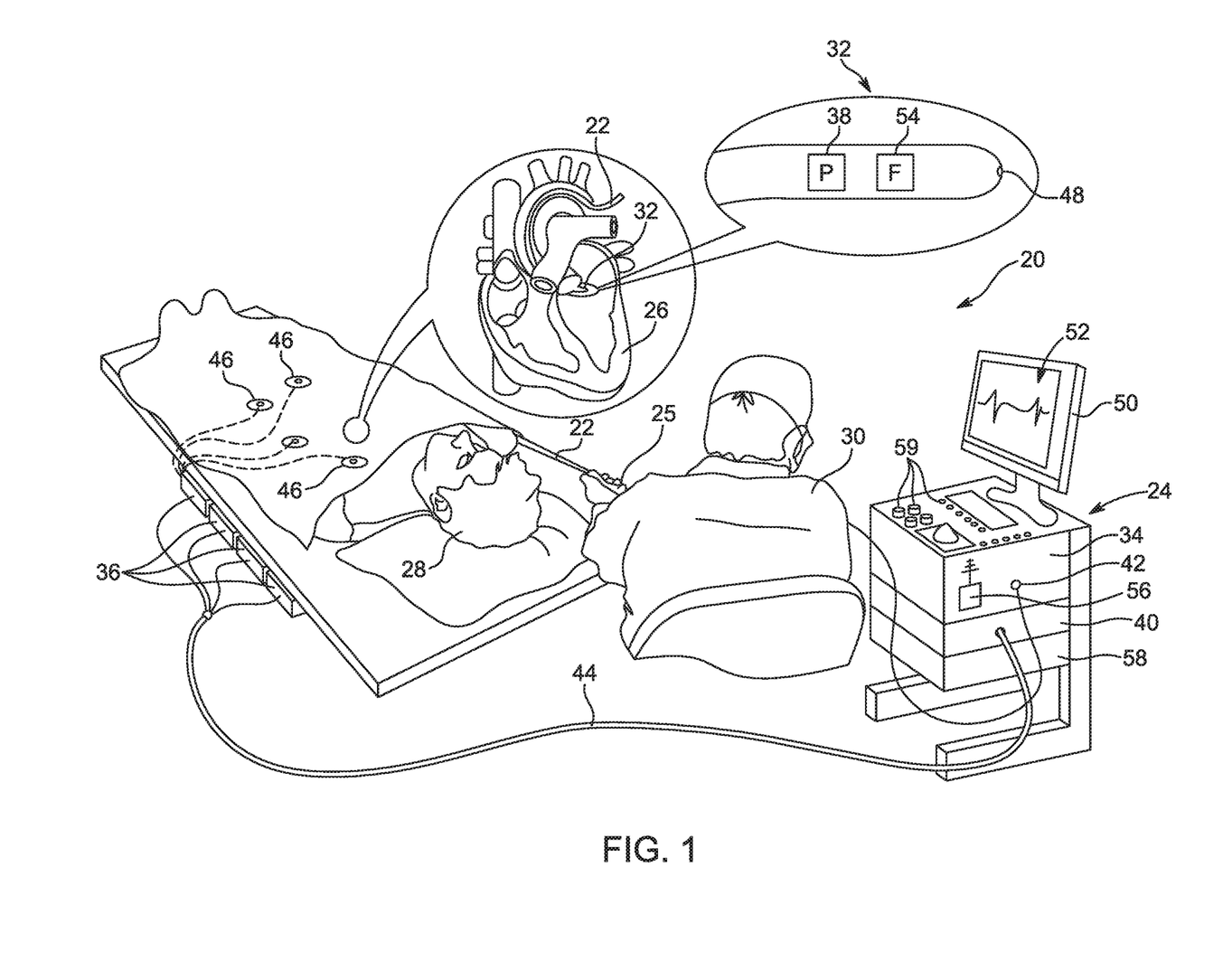
FIG. 1 is an example schematic, pictorial illustration of a medical system for conducting medical diagnostics and other procedures in accordance with the teachings of the present invention.

FIG. 1 is an illustration of an example medical system 20 that is used to generate and display information 52 during a medical procedure and to control the deployment of various probes within a patient 28. The example system includes a probe 22, such as an intracardiac catheter, a console 24 and an associated probe control unit 25. The probe 22 can be used for diagnostic or therapeutic treatment, such as for example, mapping electrical potentials in a heart 26 of the patient 28 or performing an ablation procedure. Alternatively, the probe 22 can be used, mutatis mutandis, for other therapeutic and/or diagnostic purposes in the heart, lungs, or in other body organs and ear, nose, and throat (ENT) procedures.

A physician or other operator 30 can, for example, insert the probe 22 into the vascular system of the patient 28 using the probe control unit 25 so that a distal end 32 of the probe 22 enters a chamber of the patient's heart 26. The console 24 can use magnetic position sensing to determine position coordinates of the distal end 32 inside the heart 26 or other anatomical locations. To determine the position coordinates, a driver circuit 34 in the console 24 may drive field generators 36 to generate magnetic fields within the body of the patient 28. The field generators 36 can include coils that may be placed below the torso of the patient 28 at known positions external to the patient 28. These coils may generate magnetic fields in a predefined working volume that contains the heart 26.

Figure 2:
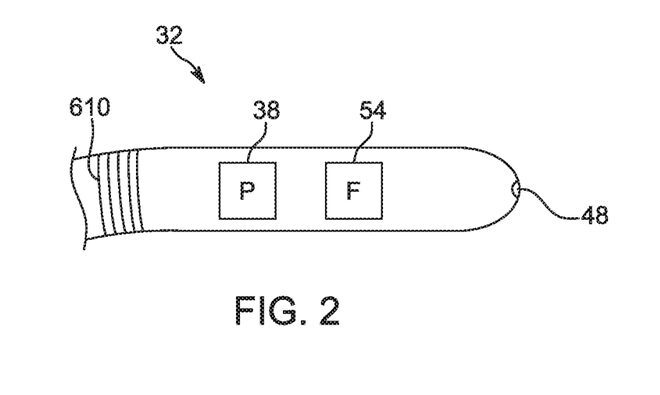
FIG. 2 is an enlarged view of the distal end of a probe made in accordance with the teachings of the present invention configured for use in the medical system of FIG. 1.

A position sensor 38 within the distal end 32 of the probe 22 can generate electrical signals in response to these magnetic fields. A signal processor 40 can process these signals in order to determine the position coordinates of the distal end 32 of the probe 22, including both location and orientation coordinates. Known methods of position sensing described hereinabove are implemented in the CARTO™ Navigation System produced by Biosense Webster Inc., of Diamond Bar, Calif., and are described in detail in the patents and the patent applications cited herein.

In this example, the position sensor 38 is configured to transmit a signal to the console 24 that is indicative of the location coordinates of the distal end 32. The position sensor 38 can, for example, comprise a type of magnetic sensor, or position transducers of other types, such as impedance-based or ultrasonic position sensors.

The probe 22 can also include a force sensor 54 contained within the distal end 32. The force sensor 54 can measure a force applied by the probe's distal end 32 to an anatomical surface of the patient 28, such as endocardial tissue of the heart 26, and generate a signal that is sent to the console 24 that corresponds to the pressure being exerted by a medical tool associated with the distal end 32 of the catheter. The amount of force sensed by the force sensor 54 can be displayed by the console 24 on an associated display 50 in, for example, units of grams of pressure.

In this example, the processor 40 is configured to receive and process the signals generated by the force sensor 54 to generate haptic level control signals corresponding to one or more predefined ranges of force. The control signals are communicated by the console 24 to a haptic feedback device, such as the device 401 illustrated in FIGS. 4A and B.

Preferably, the console 24 includes a transmitter 56 that is configured to wirelessly communicate the control signals to the haptic feedback device 401. However, a wired connection could be used to communicate the control signals. Also, the control signals can alternatively be generated by a processor disposed in the haptic feedback device 401. In which case the console 24 can communicate the force sensor's signal via the transmitter 56 to the haptic feedback device 401 to generate the control signals within the haptic feedback device itself.

At least one haptic level control signal is generated based on a range of force which is within a range of pressure exerted against an anatomical surface for proper functioning of the associated medical tool to control the haptic feedback device to exert haptic stimulation at a predetermined level that indicates an acceptable level of pressure is being exerted by the medical tool for proper operation thereof.

For example, if a particular medical tool 48 is properly operable for generating a map of electrical potentials of the heart when exerting a force in a range of 3-7 grams, a "go" control signal can be generated by the processor 40 when the signal generated by the force sensor 54 indicates a force in the 3-7 gram range. In that case, the operator 30 of the medical tool, who is wearing the haptic feedback device 401, would receive the haptic stimulation at the predetermined level and know it was safe to continue to operationally use the medical tool 48.

In lieu of the "go" control signal, being generated for the entire operational range of the example mapping tool 48, the range of force for triggering the "go" control signal can be a portion of the range. For example, where the medical tool's range of pressure for proper mapping is 3-7 grams against an anatomical surface, the "go" signal can be generated in a range of force between 3.5-6.5 grams. This permits "caution" control signals to be generated to alert the physician if the amount of pressure being exerted by the tool that was within the "go" range is approaching the minimum acceptable force, 3 grams in this example, or the maximum acceptable force, 7 grams in this example.

For this example, where the "go" signal is generated for a range of force between 3.5-6.5 grams, i.e. a portion of the tool's operable range for mapping, a "low caution" control signal can be generated when the signal generated by the force sensor 54 indicates a force of 3-3.5 grams and a "high caution" control signal can be generated when the signal generated by the force sensor 54 indicates a force of 6.5-7 grams.

The operator 30 of medical tool 48 who is wearing the haptic feedback device 401 when it receives the "low caution" control signal, would receive haptic stimulation at a level less than the predetermined level and know that the pressure being exerted by the medical tool was still acceptable, but was approaching the low end of the medical tool's range for proper functioning. An operator of medical tool who is wearing the haptic feedback device 401 when it receives the "high caution" control signal, would receive haptic stimulation at a level more than the predetermined level and know that the pressure being exerted by the medical tool was still acceptable, but was approaching the high end of the medical tool's range for proper functioning.

Additional control signals can also be generated. For the above example, a "contact" control signal can be generated when the signal generated by the force sensor 54 indicates a force of greater than 0 and less than 3 grams. A "stop/discontinue" control signal can be generated when the signal generated by the force sensor 54 indicates a force of greater than 7 grams.

The operator 30 of the medical tool 48 who is wearing the haptic feedback device 401 when it receives the "contact" control signal, would receive haptic stimulation at a level less than the level exerted for the "low caution" control signal and know that the tool 48 has contacted the anatomical surface to which it is being directed and has not yet reached the low end of the medical tool's range for proper functioning. The operator 30 of the medical tool 48 who is wearing the haptic feedback device 401 when it receives the "stop/discontinue" control signal, would receive haptic stimulation at a level more than the level exerted for the "high caution" control signal and know that the pressure being exerted by the medical tool 48 was exceeding the medical tool's range for proper functioning.

In another example where a particular medical tool 48 is properly operable for conducting an ablation of cardiac tissue of the heart when exerting a force in a range of 7-20 grams, a "go" control signal can be generated by the processor 40 when the signal generated by the force sensor 54 indicates a force in the 7-20 gram range. In that case, the operator 30 of the medical tool, who is wearing the haptic feedback device 401, would receive the haptic stimulation at the predetermined level and know it was safe to continue to operationally use the medical tool 48.

In lieu of the "go" control signal, being generated for the entire operational range of the example ablation tool 48, the range of force for triggering the "go" control signal can be a portion of the range. For example, where the ablation tool's range of pressure for proper operation is 7-20 grams against cardiac tissue, the "go" signal can be generated in a range of force between 7.5-19.5 grams. This permits "caution" control signals to be generated to alert the physician if the amount of pressure being exerted by the tool that was within the "go" range is approaching the minimum acceptable force, 7 grams in this example, or the maximum acceptable force, 20 grams in this example.

For this example, where the "go" signal is generated for a range of force between 7.5-19.5 grams, i.e. a portion of the tool's operable range for mapping, a "low caution" control signal can be generated when the signal generated by the force sensor 54 indicates a force of 7-7.5 grams and a "high caution" control signal can be generated when the signal generated by the force sensor 54 indicates a force of 19.5-20 grams.

The operator 30 of ablation tool 48 who is wearing the haptic feedback device 401 when it receives the "low caution" control signal, would receive haptic stimulation at a level less than the predetermined level and know that the pressure being exerted by the ablation tool was still acceptable, but was approaching the low end of the ablation tool's range for proper functioning. An operator of ablation tool who is wearing the haptic feedback device 401 when it receives the "high caution" control signal, would receive haptic stimulation at a level more than the predetermined level and know that the pressure being exerted by the ablation tool was still acceptable, but was approaching the high end of the ablation tool's range for proper functioning.

Additional control signals can also be generated. For the above ablation tool example, a "contact" control signal can be generated when the signal generated by the force sensor 54 indicates a force of greater than 0 and less than 7 grams. A "stop/discontinue" control signal can be generated when the signal generated by the force sensor 54 indicates a force of greater than 20 grams.

The operator 30 of the ablation tool 48 who is wearing the haptic feedback device 401 when it receives the "contact" control signal, would receive haptic stimulation at a level less than the level exerted for the "low caution" control signal and know that the ablation tool 48 has contacted the cardiac tissue to which it is being directed and has not yet reached the low end of the ablation tool's range for proper functioning. The operator 30 of the ablation tool 48 who is wearing the haptic feedback device 401 when it receives the "stop/discontinue" control signal, would receive haptic stimulation at a level more than the level exerted for the "high caution" control signal and know that the pressure being exerted by the ablation tool 48 was exceeding the tool's range for proper functioning.

Although specific types of control signals are provided as examples above, more or fewer ranges can be defined for indicating different situations to the medical tool's operator 30 related to the force exerted by the medical tool 48 against an anatomical surface.

The force sensor 54 can include a magnetic field transmitter and a receiver connected by a spring in the distal end 32, and can generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, the distal end 32 can include another type of force sensor that can use, for example, fiber optics or impedance measurements.

The probe 22 can include an electrode 48 coupled to the distal end 32 and configured to function as an impedance-based position transducer. Additionally or alternatively, the electrode 48 can be configured to measure a certain physiological property, for example the local surface electrical potential of the cardiac tissue at one or more of the multiple locations. The electrode 48 can also be configured to apply radio frequency (RF) energy to ablate endocardial tissue in the heart 26.

Although the example medical system 20 can be configured to measure the position of the distal end 32 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126 and 5,944,022, and are incorporated herein by reference as if fully set forth.

The signal processor 40 can be included in a general-purpose computer, with suitable front end and interface circuits for receiving signals from the probe 22 and controlling the other components of the console 24. The signal processor 40 can be programmed, using software, to carry out the functions that are described herein. The software can be downloaded to the console 24 in electronic form, over a network, for example, or it can be provided on non-transitory tangible media, such as optical, magnetic or electronic memory media. Alternatively, some or all of the functions of the signal processor 40 can be performed by dedicated or programmable digital hardware components.

In the example of FIG. 1, the console 24 is also connected by a cable 44 to external sensors 46. The external sensors 46 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic position sensors to locate the probe 22 during use. Although not shown in FIG. 1, the external sensors 46 can be embedded in a vest that is configured to be worn by the patient 28. The external sensors 46 can aid in identifying and tracking the respiration cycle of the patient 28. The external sensors 46 are connected to transmit information to the console 24 via the cable 44.

During a diagnostic treatment, the signal processor 40 can display the information 52 on the display 50 and/or can store data representing the information 52 in a memory 58. The memory 58 can include any suitable volatile and/or non-volatile memory, such as random access memory or a hard disk drive.

The probe control unit 25 can be configured to be operated by the physician 30 to manipulate the probe based on the information 52 which is selectable using one or more input devices 59. Alternatively, the medical system 20 can include a second operator that manipulates the console 24 while the physician 30 operates the probe control unit 25 to manipulate the probe 22 based on the displayed information 52 and the haptic stimulation provided by the haptic feedback device 401.

Figure 4A:
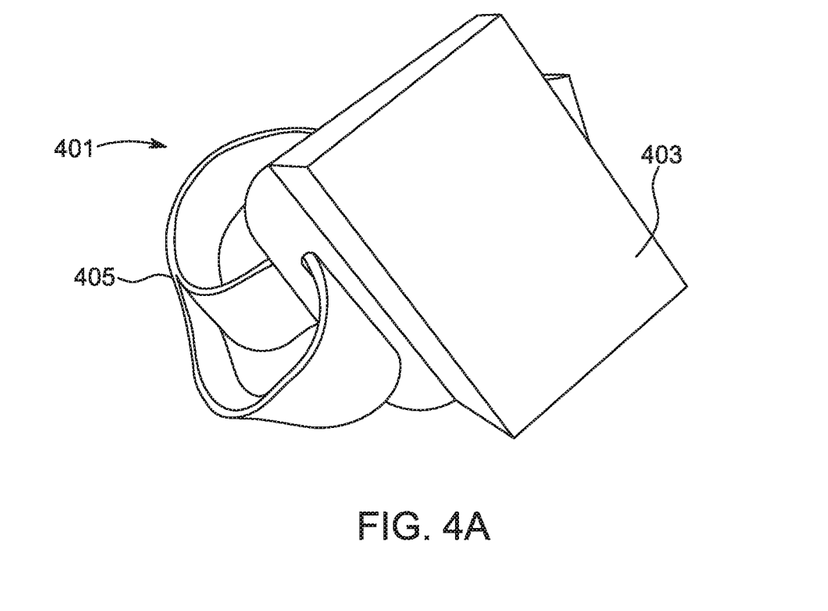
FIG. 4A is a perspective view of an example haptic feedback device for providing haptic feedback in the medical system of FIG. 1.
Figure 4B:
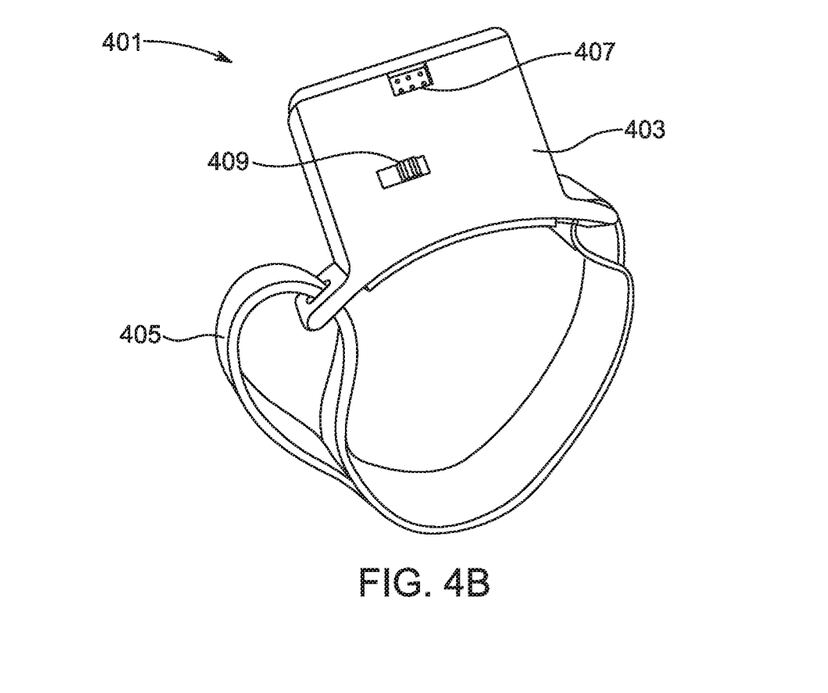
FIG. 4B is a side view of the example haptic feedback device of FIG. 4A.

With reference to FIGS. 4A and B, an example haptic feedback device 401 is configured with a housing 403 and an adjustable strap 405 that serves as a fastener to fasten the haptic feedback device 401 to a desired position on the medical system operator 30. In this case, the strap 405 includes Velcro® type of fastening configuration for securing the haptic feedback device 401 on one of the operator's wrists. The strap may use alternative fastening configurations including, but not limited to, elastic, rubber, metal mesh, leather or nylon straps and buckle or folding clasps. Preferably, the haptic feedback device 401 is battery operated and includes a re-charging port 407 and a switch 409 to turn the device off and on.

Figure 5:
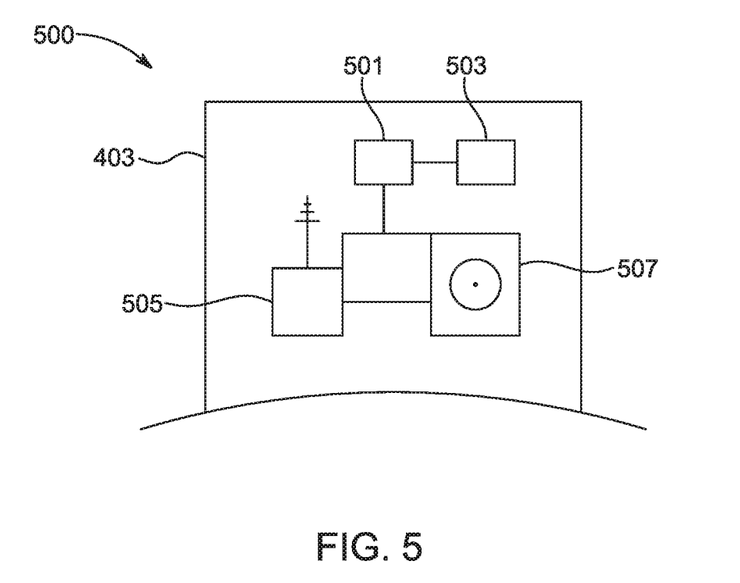
FIG. 5 is a schematic diagram of a vibration type embodiment of the example haptic feedback device of FIG. 4A.

FIG. 5 provides a schematic diagram of a vibrating version 500 of the example haptic feedback device 401 that is configured to exert different levels/rates of vibration as the haptic stimulation. The vibrating embodiment 500 includes a re-chargeable battery 501 and an associated charging device 503 that includes the re-charging port 407 shown in FIG. 4B. The battery is configured to power a wireless receiver 505 and a controllable vibrator 507 when the switch 409 is in an "on" position. The wireless receiver 505 serves as a signal input and is configured to receive the haptic level control signals from the console 24 to control the vibrator 507 to provide different levels of vibrations corresponding to the received control signals. For example, the vibrator 507 is configured to provide a different level of vibration when receiving each of the above discussed "contact," "low caution," "go," "high caution" and "stop/discontinue" control signals, from a series of increasing levels of vibration where the slowest vibration is with respect to the "contact" control level and the fastest vibration is with respect to the "stop/discontinue" control signal.

The wireless component 505 of the haptic feedback device 500 as well as the wireless component 56 of the medical system console 24 may both be configured as transceivers to communicate bi-directionally. Preferable the transceiver configuration is such that continuity signals from the haptic feedback device 500 to the medical system console 24 can be communicated to indicate that the haptic feedback device 500 is properly working during a medical procedure. This indication can be reflected on the display 50 of the medical system console 24 or via indicator lights on the medical system console 24 and/or the haptic feedback device 500 itself.

Figure 6:
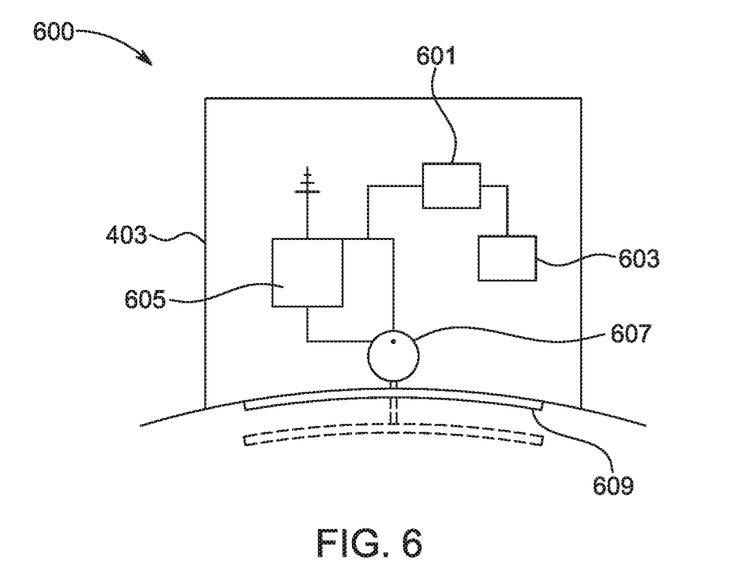
FIG. 6 is a schematic diagram of a pressure type embodiment of the example haptic feedback device of FIG. 4A.

FIG. 6 provides a schematic diagram of pressure exertion version 600 of the example haptic feedback device 401 that is configured to exert different levels of pressure as the haptic stimulation. The pressure exertion embodiment 600 includes a re-chargeable battery 601 and an associated charging device 603 that includes the re-charging port 407 shown in FIG. 4B. When the switch 409 is in an "on" position, the battery is configured to power a wireless receiver 605 and a controllable drive mechanism 607, such as a stepper motor, that is configured to drive a pressure applicator, such a pressure plate 609. The wireless receiver 605 serves as a signal input and is configured to receive the haptic level control signals from the console 24 to control the drive mechanism to provide different levels of pressure corresponding to the received signals. The wireless component 605 can be configured as a transceiver for communication of continuity signals as discussed above with respect to wireless component 505.

In this example, the drive mechanism 607 controls displacement of the pressure plate 609 in increments away from or back towards the bottom of the housing 403. Accordingly, when the haptic feedback device 401 is secured to a wrist of the operator 30, the pressure plate will exert different levels of pressure against the operator's wrist due to the extension or retraction of the pressure plate with respect to the housing 403. For example, the drive mechanism 607 is configured to extend or retract the pressure plate in increments to provide a different level of pressure when receiving each of the above discussed "contact," "low caution," "go," "high caution" and "stop/discontinue" control signals where the shortest extension (lowest pressure) is with respect to the "contact" control level and the longest extension (highest pressure) is with respect to the "stop/discontinue" control signal. In FIG. 6, the extension of the pressure plate to exert one of the levels of pressure is illustrated in phantom.

Another example is to use an electro-active polymer in the wrist bound haptic device or other configuration to apply pressure that is electrically driven. Alternatively, an inflatable sleeve such as those employed in sphygmomanometers, or other inflatable device can be employed to exert different levels of pressure as haptic stimulation.

Multiple haptic devices can be combined, such as a haptic device 500 configured to exert vibration as shown in FIG. 5 in combination with an electro-active polymer wrist band configured to exert pressure where different levels of haptic stimulation can be defined by differing levels of vibration, differing levels of pressure and/or combinations thereof. Another non-limiting alternative is to include the vibrator 507 of the vibrating embodiment 500 in the pressure exertion embodiment 600 to enable selected combinations of haptic feedback to be indicated by vibration levels, pressure levels and/or a combination of vibration and pressure levels.

The above examples are non-limiting and other configurations of the haptic feedback device and placement of one or more haptic stimulation mechanisms therein are within the scope of the invention.

The above-described medical system employing haptic feedback is advantageously employed in a variety of medical procedures. One option for treating cardiac arrhythmias can be an interventional catheter based procedure. An interventional catheter based procedure can involve a technique referred to as cardiac ablation. In such a procedure, a catheter may be advanced from the groin area of a patient into the heart. Once in place, radio frequency (RF) energy can be delivered through the catheter along a specified path of a cardiac surface within a chamber of the subject's heart with the goal of re-establishing proper heart conduction.

For conducting an example cardiac ablation, the medical tool 48 coupled to the distal end 32 of the catheter probe 33 is an electrode 48 configured to function to apply radio frequency (RF) energy to ablate endocardial tissue in the heart 26, usually while the heart is beating. For proper functioning of the electrode in the ablation of the cardiac tissue along the specified path, contact of the electrode with the cardiac surface within a specified range of pressure is required, for example in a range of 7-20 grams of pressure. The exerted pressure is controlled in part by the physician operating the catheter probe, but can also fluctuate due to the beating of the patient's heart.

Figure 3A:
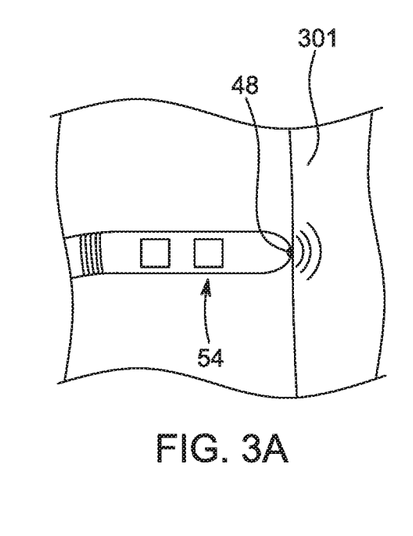
FIGS. 3A-C are a series of schematic views of the distal end of the catheter probe making contact of varying pressure with target cardiac tissue during an ablation procedure.
Figure 3B:
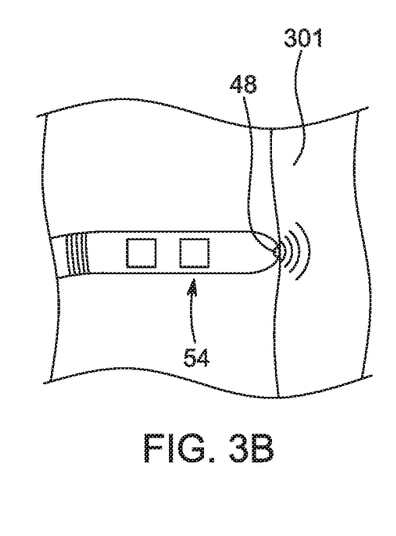
Figure 3C:
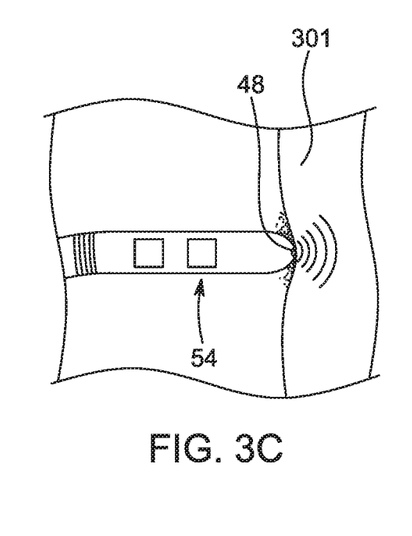

FIG. 3A illustrates the commencement of an example cardiac ablation where the ablation electrode 48 initially contacts the cardiac surface 301 to be ablated. FIG. 3B illustrates the advancement of the ablation electrode 48 to a position that exerts a force on the cardiac surface 301 at a minimum ablation pressure, for example 7 grams, for proper functioning of the ablation electrode 48 during the cardiac ablation. FIG. 3C illustrates the advancement of the ablation electrode 48 to a position that exerts a force on the cardiac surface 301 at the maximum pressure, for example 20 grams, for proper functioning of the ablation electrode 48 during the cardiac ablation.

While the probe is moved during the example ablation procedure, the force sensor 54 continuously sends signals indicating the amount of force being exerted by the ablation electrode 48 on the cardiac surface 301. While the ablation electrode 48 is in contact with the cardiac surface 301 during the cardiac ablation, but is not exerting at least the minimum force for proper functioning of the ablation electrode, as seen in FIG. 3A, the haptic feedback device 401 receives the "contact" control signal discussed above from the console 42 to exert a minimal haptic stimulation to the physician 30 thereby alerting the physician to continue to increase the pressure exerted by the ablation electrode 48 on the cardiac surface 301 to the proper functional range before commencing ablation.

While the ablation electrode 48 is in contact with the cardiac surface 301 during the cardiac ablation procedure and is exerting a force in the range for proper functioning of the ablation electrode, the haptic feedback device 401 receives the "go," "low caution," or "high caution" control signals and exerts, as discussed above, the predetermined level of haptic stimulation, or a slightly lower or greater level, respectively, to the physician 30 thereby indicating to the physician that the ablation electrode 48 can be operated to properly ablate the cardiac surface 301 along the specified path.

When the ablation electrode 48 exerts a force on the cardiac surface 301 that is higher than the range for proper functioning of the ablation electrode, the haptic feedback device 401 receives the "stop/discontinue" control signal and exerts, as discussed above, a level of haptic stimulation greater than the "high caution" level thereby indicating to the physician 30 that excessive force is being exerted by the ablation electrode 48 to the cardiac surface 301.

A further higher level of haptic stimulation can be provided when the ablation electrode 48 exerts a force on the cardiac surface 301 that is approaching a level that will cause injury and/or puncture, such as 70 grams or higher. In such case, the haptic feedback device 401 can receive a "full stop/injury alert" control signal and, in response, exert a level of haptic stimulation at an appropriate higher level to indicate to the physician 30 that excessive force exerted by the ablation electrode 48 is risking injury to the cardiac surface 301.

Although specific examples are provided for ranges, levels of haptic stimulation, medical tools and procedures are referenced above, they are non-limiting and other variations and modifications will be apparent to those skilled in the art and are within the scope of this disclosure.

What is claimed is:

1. A haptic feedback device configured to provide haptic feedback to an operator wearing the device at a desired position for facilitating a medical procedure that employs a medical tool that is separate from the haptic feedback device and is configured for operation while disposed at a distal end of a catheter and exerting pressure within an operational range against a surface, the medical tool including a sensor that generates a sensor signal reflecting an amount of pressure exerted by the medical tool against the surface, the haptic feedback device comprising:
   a fastener configured to secure the haptic feedback device to the desired position of the operator;
   a signal input configured to receive a signal reflective of the pressure exerted by the medical tool sensed as indicated the medical tool's sensor signal;
   a haptic exertion component configured to exert multiple levels of haptic stimulation to the operator responsive to pressure being asserted against the surface by the medical tool upon a condition that haptic feedback device is secured to the desired position by the fastener;
   the haptic feedback device configured to exert levels of haptic stimulation based on the signal received by the signal input such that:
      upon a condition that the received signal reflects a pressure being exerted by the medical tool against the surface is in a desired range that is commensurate with or within the medical tool's operational range, the exertion component exerts haptic stimulation to the operator at a predetermined level that indicates pressure of the medical tool is being exerted in the desired range;
      upon a condition that the received signal reflects a pressure being exerted by the medical tool against the surface is less than the desired range, the exertion component does not exert a level of haptic stimulation to the operator that is equal to or more than the predetermined level; and
      upon a condition that the received signal reflects a pressure being exerted by the medical tool against the surface is more than the desired range, the exertion component exerts a level of haptic stimulation to the operator that is more than the predetermined level.

2. A haptic feedback system including the haptic feedback device of claim 1, the medical tool and the catheter wherein the desired range is at least a portion of an operational range of the medical tool and the haptic feedback device is configured to control the level of haptic stimulation exerted based on the signal received by the signal input such that:
   the exertion component exerts a level of haptic stimulation to the operator that is less than the predetermined level in response a "contact" control signal that indicates a non-zero signal generated by the sensor of less the operational range; and
   the exertion component exerts a level of haptic stimulation to the operator that is more than the predetermined level in response a "stop" control signal that indicates a signal generated by the sensor of sufficient force to cause tissue damage above the operational range.

3. The haptic feedback system of claim 2 wherein the haptic exertion component is configured to exert vibration as haptic stimulation and includes a vibration component associated with the signal input, the vibration component configured to vibrate the haptic feedback device at different levels of frequency whereby the predetermined level of haptic stimulation is a predetermined level of vibration frequency provided by the vibration component.

4. The haptic feedback system of claim 2 wherein the haptic exertion component is configured to exert pressure as haptic stimulation and includes a pressure applicator connected to a drive mechanism that is configured to selectively drive the pressure applicator based on the signal received by the signal input such that when the haptic feedback device is secured to the desired position on the operator the pressure applicator is able to exert different levels of pressure to the operator whereby the predetermined level of haptic stimulation is a predetermined level of pressure exerted by the pressure applicator.

5. The haptic feedback system of claim 2 wherein the medical tool is an ablation tool at the distal end of a catheter and the desired range of pressure is a range of pressure to be applied by the ablation tool to a cardiac surface during an ablation procedure of a beating heart.

6. The haptic feedback system of claim 2 wherein the medical tool is an electric potential mapping tool at the distal end of a catheter and the desired range is a range of pressure to be applied by the medical tool to a cardiac surface during an electrical potential mapping procedure of a heart.

7. A haptic feedback system including the haptic feedback device of claim 1, the medical tool and the catheter wherein the desired range is a portion of an operational range of the medical tool and the haptic feedback device is configured to control the level of haptic stimulation exerted based on the signal received by the signal input such that:
the exertion component exerts haptic stimulation to the operator at the predetermined level in response to a "go" control signal that indicates pressure of the medical tool is being exerted in the desired range;
the exertion component exerts a level of haptic stimulation to the operator that is less than the predetermined level in response a "low caution" control signal that indicates a signal generated by the sensor of less than a low end of the desired range, but within the operational range;
the exertion component exerts a level of haptic stimulation to the operator that is more than the predetermined level in response a "high caution" control signal that indicates a signal generated by the sensor of more than a high end of the desired range, but within the operational range;
upon a condition that the received signal reflects a pressure being exerted by the medical tool against the surface is less than the operational range, the exertion component does not exert a level of haptic stimulation to the operator that is equal to or more than the level exerted in response to the "low caution" control signal; and
upon a condition that the received signal reflects a pressure being exerted by the medical tool against the surface is more than the operational range, the exertion component exerts a level of haptic stimulation to the operator that is more than the level exerted in response to the "high caution" control signal.

8. The haptic feedback system of claim 2 wherein the fastener is configured to secure the haptic feedback device to a wrist of the operator, the haptic exertion component is disposed in a housing of the device, and the fastener comprises a wrist strap configured to secure the housing to a wrist of the operator.

9. A medical system including the haptic feedback system of claim 2 and a console configured to receive the sensor signal from the pressure sensor of the medical tool and to generate and communicate to the haptic feedback device the signal reflective of the sensor signal.

10. The medical system of claim 9 wherein the signal input of the haptic feedback device includes a wireless receiver and the console includes a transmitter configured to communicate the signal reflective of the sensor signal and wherein the console includes a processor configured to process the sensor signal such that the signal reflective of the sensor signal serves as a control signal to control the level of haptic stimulation exerted by the haptic exertion component.

11. A method of using the haptic feedback device of claim 1 comprising:
securing the haptic feedback device to the desired position on the operator of the medical tool;
the operator of the medical tool employing the medical tool at the distal end of the catheter to contact the surface and to proceed with selectively operating the medical tool with respect to the contacted surface based on levels of haptic stimulation exerted by the haptic feedback device;
receiving a signal reflective of the sensor signal by the signal input;
exerting levels of haptic stimulation to the operator by the haptic exertion component based on the signal received by the signal input such that:
upon a condition that the received signal reflects a pressure being exerted by the medical tool against the surface is in the desired range, the exertion component exerts haptic stimulation to the operator at the predetermined level;
upon a condition that the received signal reflects a pressure being exerted by the medical tool against the anatomical surface of the patient is less than the desired range, the exertion component does not exert a level of haptic stimulation to the operator that is equal to or more than the predetermined level; and
upon a condition that the received signal reflects a pressure being exerted by the medical tool against the anatomical surface of the patient is more than the desired range, the exertion component exerts a level of haptic stimulation to the operator that is more than the predetermined level; and
exerting additional levels of haptic stimulation based on the signal received by the signal input responsive to pressure being asserted against the surface by the medical tool during the medical procedure including:
a level of haptic stimulation that is less than the predetermined level in response a "low caution" control signal that indicates a signal generated by the sensor within a lowest portion of the operational range of the medical tool and a level of haptic stimulation that is more than the predetermined level in response a "high caution" control signal that indicates a signal generated by the sensor within a highest portion of the desired range; or
a level of haptic stimulation that is less than the predetermined level in response a "contact" control signal that indicates a non-zero signal generated by the sensor of less the operational range and a level of haptic stimulation to the operator that is more than the predetermined level in response a "stop" control signal that indicates a signal generated by the sensor of sufficient force to cause damage to the surface above the operational range.

12. The method of claim 11 wherein the fastener secures the haptic feedback device to a wrist of the operator.

13. The method of claim 11 wherein the haptic exertion component is configured to exert vibration as haptic stimulation and includes a vibration component associated with the signal input that vibrates the haptic feedback device at different levels of frequency whereby the predetermined level of haptic stimulation is a predetermined level of vibration frequency provided by the vibration component.

14. The method of claim 11 wherein the haptic exertion component is configured to exert pressure as haptic stimulation and includes a pressure applicator connected to a drive mechanism that drives the pressure applicator based on the signal received by the signal input such that the pressure applicator exerts different levels of pressure to the wrist of the operator whereby the predetermined level of haptic stimulation is a predetermined level of pressure exerted by the pressure applicator.

15. The method of claim 11 wherein the medical tool is an ablation tool at the distal end of a catheter and the desired range of pressure is a range of pressure to be applied by the ablation tool to a cardiac surface during an ablation procedure of a beating heart.

16. The method of claim 11 wherein the medical tool is an electric potential mapping tool at the distal end of a catheter and the desired range of pressure is a range of pressure to be applied by the medical tool to a cardiac surface during an electrical potential mapping procedure of a patient's heart.

17. The method of claim 11 wherein the haptic feedback device controls the level of haptic stimulation exerted based on the signal received by the signal input such that:
the exertion component exerts haptic stimulation to the operator at the predetermined level in response to a "go" control signal that indicates pressure of the medical tool is being exerted in the desired range;
the exertion component exerts a level of haptic stimulation to the operator that is less than the predetermined level in response a "low caution" control signal that indicates a signal generated by the sensor of less than a low end of the desired range, but within the operational range;
the exertion component exerts a level of haptic stimulation to the operator that is more than the predetermined level in response a "high caution" control signal that indicates a signal generated by the sensor of more than a high end of the desired range, but within the operational range;
upon a condition that the received signal reflects a pressure being exerted by the medical tool against the anatomical surface of the patient is less than the operational range, the exertion component does not exert a level of haptic stimulation to the operator that is equal to or more than the level exerted in response to the "low caution" control signal; and
upon a condition that the received signal reflects a pressure being exerted by the medical tool against the anatomical surface of the patient is more than the operational range, the exertion component exerts a level of haptic stimulation to the operator that is more than the level exerted in response to the "high caution" control signal.

18. The method of claim 11 wherein the haptic feedback device controls the level of haptic stimulation exerted based on the signal received by the signal input such that:
the exertion component exerts a level of haptic stimulation to the operator that is less than the predetermined level in response a "contact" control signal that indicates a non-zero signal generated by the sensor of less the operational range; and
the exertion component exerts a level of haptic stimulation to the operator that is more than the predetermined level in response a "stop" control signal that indicates a signal generated by the sensor of sufficient force to cause tissue damage above the operational range.

19. The method of claim 11 wherein a console receives the sensor signal from the pressure sensor of the medical tool and generates and wirelessly communicates the signal reflective of the sensor signal to the haptic feedback device.

20. The method of claim 11 wherein the sensor signal is processed by a processor to generate the signal reflective of the sensor signal such that the signal reflective of the sensor signal serves as a control signal to control the level of haptic stimulation exerted by the haptic exertion component.

* * * * *

UNITED STATES PATENT AND TRADEMARK OFFICE
CERTIFICATE OF CORRECTION

PATENT NO. : 10,932,876 B2
APPLICATION NO. : 16/117961
DATED : March 2, 2021
INVENTOR(S) : Dror Shlomo Levy et al.

It is certified that error appears in the above-identified patent and that said Letters Patent is hereby corrected as shown below:

On the Title Page
In Item (72), under "Inventors", in Column 1, Line 4, delete "Zichron Yaakov (IL);" and insert -- Zikhron Ya'akov (IL); --, therefor.

In the Specification
In Column 2, Line 57, delete "less the" and insert -- less than the --, therefor.
In Column 9, Line 65, delete "such a pressure" and insert -- such as a pressure --, therefor.

In the Claims
In Column 12, Lines 47-48, in Claim 2, delete "less the" and insert -- less than the --, therefor.
In Column 14, Line 53, in Claim 11, delete "less the" and insert -- less than the --, therefor.
In Column 16, Lines 21-22, in Claim 18, delete "less the" and insert -- less than the --, therefor.

Signed and Sealed this
Seventh Day of February, 2023

Katherine Kelly Vidal
*Director of the United States Patent and Trademark Office*